United States Patent
Flower et al.

(10) Patent No.: US 6,443,976 B1
(45) Date of Patent: Sep. 3, 2002

(54) METHODS FOR TREATING CONDITIONS AND ILLNESSES ASSOCIATED WITH ABNORMAL VASCULATURE

(75) Inventors: Robert W. Flower, Hunt Valley, MD (US); Abu Alam, Lake Forest, IL (US)

(73) Assignee: Akorn, Inc., Buffalo Grove, IL (US)

( * ) Notice: Subject to any disclaimer, the term of this patent is extended or adjusted under 35 U.S.C. 154(b) by 0 days.

(21) Appl. No.: 09/452,117

(22) Filed: Nov. 30, 1999

(51) Int. Cl.[7] ............................................. A61N 33/00
(52) U.S. Cl. ........................ 607/88; 607/89; 606/2; 606/4; 600/101; 600/108; 604/20; 604/21; 604/508
(58) Field of Search ..................... 604/500, 507, 604/508, 20, 21, 22; 600/1, 4, 3, 101, 104, 108; 606/2, 4, 10, 13, 15; 607/1, 88, 89, 100, 104; 128/898

(56) References Cited

U.S. PATENT DOCUMENTS

| | | | |
|---|---|---|---|
| 1,048,419 A | | 12/1912 | Krumbiegel et al. |
| 2,895,955 A | | 7/1959 | Heseltine et al. |
| 3,736,524 A | | 5/1973 | Drexhage |
| 3,871,772 A | | 3/1975 | Munnerlyn et al. |
| 3,893,447 A | | 7/1975 | Hochheimer et al. |
| 3,944,341 A | | 3/1976 | Pomerantzeff |
| 4,056,310 A | | 11/1977 | Shimizu et al. |
| 4,251,139 A | | 2/1981 | Matsumura |
| 4,336,809 A | * | 6/1982 | Clark .................. 600/478 |
| 4,369,250 A | | 1/1983 | Gindler |
| 4,412,543 A | | 11/1983 | Vassiliadis et al. |
| 4,466,442 A | | 8/1984 | Hilmann et al. |
| 4,541,438 A | | 9/1985 | Parker et al. |
| 4,573,778 A | | 3/1986 | Shapiro |
| 4,608,990 A | | 9/1986 | Elings |
| 4,762,701 A | | 8/1988 | Horan et al. |
| 4,786,813 A | | 11/1988 | Svanberg et al. |
| 4,799,783 A | | 1/1989 | Takahashi et al. |
| 4,821,117 A | | 4/1989 | Sekiguchi |
| 4,835,103 A | | 5/1989 | Cercek et al. |
| 4,842,401 A | | 6/1989 | Maurice |
| 4,859,584 A | | 8/1989 | Horan et al. |
| 4,978,213 A | | 12/1990 | El Hage |
| 5,072,731 A | | 12/1991 | Taratuta et al. |
| 5,092,331 A | | 3/1992 | Nakamura et al. |
| 5,116,114 A | | 5/1992 | Nakamura |
| 5,126,235 A | | 6/1992 | Hioki |
| 5,141,303 A | | 8/1992 | Yamamoto et al. |
| 5,150,292 A | | 9/1992 | Hoffmann et al. |
| 5,163,437 A | | 11/1992 | Fujii et al. |
| 5,225,859 A | | 7/1993 | Fleischman |
| 5,247,318 A | | 9/1993 | Suzuki |
| 5,277,913 A | | 1/1994 | Thompson et al. |
| 5,279,298 A | | 1/1994 | Flower |
| RE34,544 E | * | 2/1994 | Spears .................. 604/20 |
| 5,292,362 A | | 3/1994 | Bass et al. |
| 5,303,709 A | | 4/1994 | Dreher et al. |
| 5,315,998 A | | 5/1994 | Tachibana et al. |
| 5,394,199 A | | 2/1995 | Flower |
| 5,400,791 A | | 3/1995 | Schlier et al. |
| 5,438,989 A | | 8/1995 | Haglund et al. |
| 5,441,858 A | | 8/1995 | Delprato et al. |
| 5,450,144 A | | 9/1995 | Ben Nun |
| 5,552,452 A | | 9/1996 | Khadem et al. |
| 5,569,587 A | | 10/1996 | Waggoner et al. |
| 5,573,750 A | | 11/1996 | Singh |
| 5,576,013 A | | 11/1996 | Williams et al. |
| 5,618,733 A | | 4/1997 | Sakata et al. |
| 5,624,597 A | | 4/1997 | Buhl et al. |
| 5,632,767 A | * | 5/1997 | Sinofsky .................. 606/15 |

(List continued on next page.)

FOREIGN PATENT DOCUMENTS

| | | |
|---|---|---|
| DE | 3124305 | 1/1983 |
| DE | 244492 | 4/1987 |
| DE | 3926652 | 4/1991 |
| EP | 0109846 | 5/1984 |
| EP | 0554643 | 8/1993 |
| EP | 0649667 | 4/1995 |
| EP | 0791361 A | 8/1997 |
| EP | 589825 | 5/1998 |
| EP | 0933096 | * 8/1999 |
| GB | 1048419 | 11/1966 |
| GB | 2034916 | 6/1980 |
| JP | 87042892 | 9/1987 |
| WO | WO 9524930 A | 9/1995 |
| WO | 95/24930 | 9/1995 |
| WO | 96/31237 | 12/1996 |
| WO | 97/31582 | 9/1997 |
| WO | WO 9733619 A | 9/1997 |
| WO | 97/33620 | 9/1997 |
| WO | 97/46262 A | 12/1997 |
| WO | WO 9825648 A | 6/1998 |
| WO | 00/41726 A | 7/2000 |
| WO | WO 0126591 A | 4/2001 |

OTHER PUBLICATIONS

Wu, Lihteh, MD., Neovascularization, Choroidal; eMedicine Journal, Apr. 27, 2001, vol. 2, No. 4. (http://www.e-medicine.com/oph/topic534.htm).*

Reichel E. MD et al, "Indocyanine Green Dye–Enhanced Diode Laser Photocoagulation of Poorly Defined Subfoveal Choroidal Neovascularization", Ophthalmic Surgery 25, 195–201. (1994).*

(List continued on next page.)

Primary Examiner—Brian L. Casler
Assistant Examiner—Jeremy Thissell
(74) Attorney, Agent, or Firm—Leydig, Voit & Mayer, Ltd.

(57) ABSTRACT

Use of radiation-absorbing dyes (e.g., indocyanine green (ICG), fluorescein, rose bengal) and photodynamic dyes (e.g., hematoporphyrins, aminolevulinic acids, porphyrins, merocyanines, porphycenes, porfimer sodium, verteporfin, Photofrin II, PH-10, chlorins, zinc phthalocyanine, purpurins, pheophorbides, monoclonal antibody-dye conjugates of any of the foregoing dyes) for the treatment of conditions associated with abnormal vasculature, including, generally, lesions, and, more specifically, tumors (cancerous and benign) and choroidal neovascularization (CNV) associated with age-related macular degeneration (ARMD).

41 Claims, No Drawings

U.S. PATENT DOCUMENTS

| | | | |
|---|---|---|---|
| 5,643,356 A | | 7/1997 | Nohr et al. |
| 5,648,062 A | | 7/1997 | Klaveness et al. |
| 5,676,928 A | | 10/1997 | Klaveness et al. |
| 5,691,204 A | | 11/1997 | Kantor et al. |
| 5,707,608 A | | 1/1998 | Liu |
| 5,707,986 A | | 1/1998 | Miller et al. |
| 5,716,642 A | | 2/1998 | Bagchi et al. |
| 5,719,027 A | | 2/1998 | Miyazaki et al. |
| 5,747,475 A | | 5/1998 | Nordquist et al. |
| 5,750,722 A | | 5/1998 | Huynh et al. |
| 5,762,957 A | | 6/1998 | Mehlhorn |
| 5,773,299 A | | 6/1998 | Kim et al. |
| 5,798,349 A | | 8/1998 | Levy et al. |
| 5,804,448 A | | 9/1998 | Wang et al. |
| 5,847,002 A | * | 12/1998 | Willoughby et al. ........ 514/561 |
| 5,908,415 A | * | 6/1999 | Sinofsky ...................... 606/15 |
| 6,022,309 A | * | 2/2000 | Celliers et al. ................ 600/7 |
| 6,028,099 A | * | 2/2000 | de Juan, Jr. ................ 514/434 |
| 6,316,007 B1 | * | 11/2001 | Nordquist et al. ....... 424/184.1 |
| 6,319,273 B1 | * | 11/2001 | Chen et al. .................. 128/898 |
| 6,351,663 B1 | * | 2/2002 | Flower et al. ........... 250/459.1 |

OTHER PUBLICATIONS

Mendelsohn et al. "Amelioration of Experimental Lipid Keratopathy by Photochemically Induced Thrombosis of Feeder Vessels," *Archives of Ophthalmology*, vol. 105, No. 7; p. 983–988; Jul. 1987.

Nirankari, Verinder S. "Lawer Photocoagulation for Corneal Stromal Vascularization," *Transactions of the American Ophthalmological Society Annual Meeting*, CA, Toronto, vol. 90; p. 595–669; 1992.

Shiraga et al. "Feeder Vessel Photocoagulation of Subfoveal Choroidal Neovascularization Secondary to Age–Related Macular Degeneration," *Ophthalmology*, US, J. B. Lippincott Co., Philadelphia, PA, vol. 105, No. 4; p. 662–669; Apr. 4, 1998.

International Search Report (Jul. 31, 2001).

Mendelson et al., "Amelioration of Experimental Lipid Keratopathy by Photochemically Induced Thrombosis of Feeder Vessels," *Arch Ophthalmol*, vol. 105, Jul. 1987 (pp. 983–988).

Tsilimbaris et al., "Photothrombosis Using Two Different Phthalocyanine Administration Routes: Continuous I.V. Infusion v. Bolus I.V. Injection," *Photochem. Photobiol.*, 62(3), 1995, (pp. 435–441).

Spinelli et al., "Endoscopic Treatment of Gastrolintestinal Tumors: Indications and Results of Laser Photocoagulation and Photodynamic Therapy," *Seminars in Surgical Oncology*, 11 (4), 1995, (pp. 307–318) (Abstract only).

Von Kerczek et al., "The Effects of Indocyanine Green Dye–Enhanced Photocoagulation on the Blood Flow in the Choriocapillaris and the Choroidal Neovascularization," *Advances in Heat and Mass Transfer in Biotechnology*, 2000, (pp. 1–3). (Abstract only).

Flower et al., "Clinical Infrared Absorption Angiography of the Choroid," *American Journal of Ophthalmology*, vol. 73, No. 3, pp. 458–459 (1972).

Flower et al., "A Clinical Technique and Apparatus for Simultaneous Angiography of the Separate Retinal and Choroidal Circulations," Investigative Ophthalmology, vol. 12(4), pp. 248–261 (1973).

Hochheimer et al., "Angiography of the Cervix," *Johns Hopkins Medical Journal*, vol. 135, pp. 375–382, (1974).

Flower, "High Speed Human Choroidal Angiography Using Indocyanine Green Dye and a Continuous Light Source," *International Symposium on Fluorescein Angiography, Documenta Ophthmologica* Proceedings Series, vol. 9, pp. 59–64 (1976).

Flower et al., "Indocyanine Green Dye Fluorescence and Infrared Absorption Choroidal Angiography Performed Simultaneously with Fluorescein Angiography," *Johns Hopkins Medical Journal*, vol. 138, No. 2, pp. 33–42 (1976).

Orth et al., "Potential Clinical Applications of Indocyanine Green Choroidal Angiography," *The Eye, Ear, Nose and Throat Monthly*, vol. 55, Jan., pp. 15–28 (1976).

Patz et al., "Clinical Applications of Indocyanine Green Angiography," *International Symposium on Fluorescein Angiography, Documenta Ophthmologica*, vol. 9, pp. 245–251 (1976).

Flower, "Choroidal Fluorescent Dye Filling Patterns a Comparison of High Speed Indocyanine Green and Fluorescein Angiograms," *International Ophthalmology*, vol. 2(3), pp. 143–150 (1980).

Hyvarinen et al., "Indocyanine Green Fluorescence Angiography," *ACTA Ophthalmologica*, vol. 58, pp. 528–538 (1980).

Bischoff et al., "Ten Years Experience with Choroidal Angiography Using Indocyanine Green Dye–A New Routine Examination or an Epilogue," *Doc Ophthalmology*, vol. 60(3), pp. 235–291 (1985).

Murphy et al., "Effects of Retinal Photocoagulation on the Choroidal Circulation," *Investigative Ophthalmology & Visual Science*, vol. 32(4), p. 785 (1991) Meeting Abstract.

Murphy et al., "Indocyanine Green Angiographic Studies of Accult Choroidal Neovascularization," *Investigative Ophthalmology & Visual Science*, vol. 34(4), p. 1134 (1993) Meeting Abstract.

Flower, "Binding and Extravasation of Indocyanine Green Dye," *Retina*, vol. 14, No. 13, pp. 283–284 (1994).

Lim et al., "Indocyanine Green Angiography," *International Ophthalmology Clinics*, vol. 35(4), pp. 59–70 (1995).

Hiner et al., "A Previously Undescribed Indocyanine Green Angiographic Filling Pattern," *Investigative Ophthalmology & Visual Science*, vol. 36, No. 4, p. S243 (1995) Meeting Abstract.

Flower et al., "Disparity Between Fundus Camera and Scanning Laser Ophthalmoscope Indocyanine Green Imaging of Retinal Pigment Epithelium Detachments," *Retina*, vol. 18(3), pp. 260–268 (1998).

Staurenghi et al., "Laser Treatment of Feeder Vessels in Subfoveal Choroidal Neovascular Membranes," *Ophthalmology*, vol. 105, No. 12, pp. 2297–2305 (1998).

Flower et al., "Expanded Hypothesis on the Mechanism of Photodynamic Therapy Action on Choroidal Neovascularization," *Retina*, vol. 19, No.5 pp. 365–369 (1999).

Flower, "Experimental Studies of Indocyanine Green Dye–Enhanced Photocoagulation of Choroidal Neovascularization Feeder Vessels," *American Journal of Ophthalmology* vol. 129, No. 4, pp. 501–512 (2000).

"Photosensitizer," *Ophthamalmic Surgery and Lasers*, vol. 28, No. 5, p 410 (1997).

Desmettre et al., "Diode Laser–Induced Thermal Damage Evaluation on the Retina with a Liposome Dye System," *Lasers in Surgery and Medicine*, vol. 24, pp. 61–68 (1999).

Flower et al., "Evolution of Indocyanine Green Dye Choroidal Angiography," *Optical Engineering*, vol. 34, No. 3, pp. 727–736 (1995).

Flower et al., "Pulsatile Flow in the Choroidal Circulation: A Preliminary Investigation," *EYE,* vol. 4, pp. 310–318 (1990).

Flower et al., "Variability in Choriocapillaris Blood Flow Distribution," *Investigative Ophthalmology & Visual Science,* vol. 36, No. 7, pp. 1247–1258 (1995).

Flower, "Choroidal Angiography Today and Tomorrow," *Retina,* vol. 12, No. 3, pp. 189–190 (1992).

Flower, "Extraction of Choriocapillaris Hemodynamic Data from ICG Fluorescence Angiograms," *Investigative Ophthalmology & Visual Science,* vol. 34, No. 9, pp. 2720–2729 (1993).

Flower, "Injection Technique for Indocyanine Green and Sodium Fluorescein Dye Angiography of the Eye," *Investigative Ophthalmology,* vol. 12, No. 12, pp. 881–895 (1973).

Gathje et al., "Stability Studies on Indocyanine Green Dye," *Journal of Applied Physiology,* vol. 29, No. 2, pp. 181–185 (1970).

Holzer et al., "Photostability and Thermal Stability of Indocyanine Green," *J. Photochem. Photobiol. B: Biol.,* vol. 47, pp. 155–164 (1998).

Klein et al., "An Image Processing Approach to Characterizing Choroidal Blood Flow," *Investigative Ophthalmology & Visual Science,* vol. 31, No. 4, pp. 629–637 (1990).

Miki et al., "Computer Assisted Image Analysis Using the Subtraction Method in Indocyanine Green Angiography," *European Journal of Ophthalmology,* vol. 6, No. 1, pp. 30–38 (1996).

DuBosar, "Population at Risk: Age–Related Macular Degeneration," *Ocular Surgery News,* 10 Pages, (May 15, 1998).

Chen et al., "Photothermal Effects on Murine Mammary Tumors Using Indocyanine Green and an 808–nm Diode Laser: an in vivo Efficacy Study," *Cancer Lett.,* vol. 98, No. 2, pp. 169–173 (1996).

Alcon Pharmaceuticals Ltd. "Pharmacyclics Inc," *The Business and Medicine Report,* p. 63 (Jan. 1998).

Shiraga et al., "Feeder Vessel Photocoagulation of Subfoveal Choroidal Neovascularization Secondary to Age–Related Macular Degeneration," *Ophthalmology,* vol. 105, No. 4, pp. 662–669 (1998).

* cited by examiner

METHODS FOR TREATING CONDITIONS AND ILLNESSES ASSOCIATED WITH ABNORMAL VASCULATURE

FIELD OF THE INVENTION

The present invention relates generally to methods for treating harmful conditions and illnesses associated with abnormal vasculature.

BACKGROUND OF THE INVENTION

Abnormal vasculature in a body is typically associated with a lesion. Lesions are generally defined as an abnormal tissue structure located in an organ or other body part, and are often a manifestation of a harmful condition, disease or illness. Lesions may take many specific forms, e.g., choroidal neovascularization (CNV) found in the eye, and tumors, both benign and malignant, located in organs and other parts of the body.

CNV is one manifestation of Age-Related Macular Degeneration (AMRD). AMRD is a leading cause of significant visual impairment in the elderly. CNV originates in the choroidal blood vessels of the eye which lie adjacent the retina. When a CNV forms, it may intrude into and displace a portion of the retina from its normal position, thereby distorting vision. Timely diagnosis and treatment of a CNV is an important therapeutic objective because permanent vision loss can result if hemorrhage of the CNV occurs.

Common methods of treating abnormal vasculature use laser technology. One example of such methods, used in the treatment of CNV, is photodynamic therapy (PDT). The object of PDT is to permit selective destruction of undesirable tissue without damaging surrounding healthy tissue. This is possible because the photodynamic dyes used in PDT are selectively retained in the area to be treated. For example, in the case of CNV, the photodynamic dye selectively binds to the proliferating endothelium in the CNV. Similarly, in the case of tumors, the photodynamic dye remains in cancer cells for a longer period of time than in normal, healthy cells. Thus, only a general identification of the tissue to be treated need be obtained before administering PDT.

Generally, the application of PDT requires the administration of a photodynamic dye into a subject, typically by IV injection. After the dye administration is completed, the dye becomes distributed throughout the body. The physician must then wait until the dye accumulates in the tissue to be treated, and the concentration of dye in the healthy tissues becomes relatively low compared to that in the tissue to be treated. When that point is reached, the dye in the tissue to be treated is subjected to radiation, e.g., light of a certain wavelength generated by a laser, causing excitation of the dye. While the precise mechanism is not fully understood, it is believed that the dye, when excited, generates oxygen radicals. These radicals attack the cells of the surrounding tissue, resulting in degranulation of those cells. By way of specific example, and in the case of a CNV, PDT destroys the endothelial cells of the CNV. This reduces, and preferably halts, the flow of blood within the CNV. In treating tumors, endoscopes are commonly used in combination with fiber optics to deliver radiation (in the form of light) of a particular wavelength (generally from about 630 nm to about 750 nm) to the tumor undergoing PDT. Radiation delivery via fiber optics is advantageous because it allows the treatment light source to be placed close to the tumor, enabling treatment of only one tumor. This delivery method is also currently required because the treatment radiation cannot pass through more than about 3 cm of tissue. One reference describing the use of PDT in cancer therapy is "The Use of PDT in Photodynamic Therapy in Oncology: Methods and Clinical Use," 85(6) J. Nat'l Cancer Inst. 443–456 (1993).

Unfortunately, PDT is not a permanent solution, particularly with respect to CNV treatment. Reperfusion following initially successful PDT on a CNV typically occurs within 4–12 weeks after treatment, requiring a subject to receive multiple retreatments. This on-going need for re-treatment is costly and inconvenient to the patient.

Further, and at least in the case of Photofrin® (a photodynamic dye used with PDT), patients experience a skin sensitivity to light after administration. More specifically, patients to whom Photofrin® has been administered must avoid direct sunlight for 4 to 6 weeks after administration, and take other related precautions, e.g., wear sunglasses and protective clothing when outdoors. In addition, surgery involving exposure of internal organs to bright surgical lights must be avoided.

A need thus exists for improved methods of treating conditions and illnesses having abnormal vasculature associated therewith, including, but not limited to, lesions, and, more specifically, CNVs and tumors.

SUMMARY OF THE INVENTION

The present invention meets the foregoing and other needs in a variety of ways. Generally, the present invention provides a method for treating a lesion, such as a CNV or tumor, in an animal. The methods of the present invention contemplate treating such a lesion by subjecting the lesion to PDT, and subjecting a blood vessel that carries blood into the lesion to thermal photocoagulation to reduce the flow of blood through that vessel and into the lesion. Regression of the lesion should follow this method of treatment.

It has been found methods of the present invention offer, among other benefits, enhanced therapeutic results and cost savings as compared to therapy consisting of PDT alone. For example, the need for PDT re-treatment is eliminated by the use of thermal photocoagulation, thereby lowering the overall cost of treatment and lessening patient inconvenience. Further, the undesirable side effects associated with PDT, e.g., skin sensitivity to light, are minimized using the inventive method.

More specifically, one aspect of the present invention includes, but is not limited to, the steps of: administering a first composition comprising a photodynamic dye and a pharmaceutically-acceptable carrier to the animal to fill at least a portion of the lesion with the first composition; applying radiation to the photodynamic dye in the lesion of a type and in an amount sufficient to excite the photodynamic dye; and applying radiation to the blood vessel that carries blood into the lesion of a type and in an amount sufficient to increase the temperature of the vessel, reducing the rate of blood flow through the vessel.

Another aspect of the present invention provides methods specific to the treatment of a CNV. In connection with the development of this aspect, it was recognized that, after PDT of a CNV was completed, and recurrence of the CNV was detected, angiograms of the CNV permitted CNV feeder vessels to be readily identified, as compared to angiograms obtained without prior PDT. Of course, once such feeder vessels are identified, thermal photocoagulation (with or without the use of a radiation-absorbing dye, the latter also referred to as dye enhanced thermal photocoagulation) can be performed with a relatively high degree of success, providing for relatively permanent treatment of the CNV.

A further aspect of the present invention provides methods specific to the treatment of a tumor in an animal. The method includes, but is not limited to, the steps of: administering a first composition comprising a photodynamic dye and a pharmaceutically-acceptable carrier to the animal to fill at least part of the tumor with the first composition; applying radiation to the photodynamic dye residing in the tumor of a type and in an amount sufficient to excite the photodynamic dye; and applying radiation to a blood vessel that carries blood into the tumor of a type and in an amount sufficient to increase the temperature of the vessel, reducing the rate of blood flow through the vessel and into the tumor.

All of the inventive aspects of the present invention as described and claimed herein may be used on animals, e.g., humans, dogs, cats, but are preferably used in connection with the diagnosis and treatment of human subjects.

The inventive methods may be expanded upon by the optional administration of other treatment steps or therapies. For example, and in connection with the treatment of tumors, the present invention may, if desired, be augmented by the administration of chemotherapeutic and/or anti-angiogenesis agents (either via IV or by direct injection into the tumor), conventional radiation therapy, or combinations thereof. If a tumor is undergoing treatment in accordance with the inventive methods, a decrease in size of the tumor after the treatment may permit successful removal of the tumor by surgery.

The foregoing and other aspects of the present invention will be more clearly understood upon reference to the following preferred embodiments.

DETAILED DESCRIPTION OF THE PREFERRED EMBODIMENTS

The methods of the present invention include a series of treatment steps. It should be understood that these methods and associated steps may be performed in any logical order. Further, the methods may be performed alone, or in conjunction with other diagnostic procedures and treatments administered before, during or after such methods without departing from the scope and spirit of the methods.

One aspect of the present invention provides a method for treating a lesion in an animal. For the method of treatment to be effective, the lesion should further have a blood vessel that carries blood into (feeds) the lesion. The inventive method includes, but is not limited to, the steps of: administering a first composition comprising a photodynamic dye and a pharmaceutically-acceptable carrier to the animal to fill at least a portion of the lesion with the first composition. After administration of the first composition, radiation is applied to the photodynamic dye that is resident in the lesion. The radiation should be of a type and in an amount sufficient to excite the photodynamic dye. When the photodynamic dye becomes excited, the lesion is damaged, and subsequently regresses.

While not being bound to any particular theory, it is believed that the mechanism of action of photodynamic dyes is as follows. When the dyes are exposed to a specific type of radiation—a specific wavelength of light, which varies from dye to dye—the dye is changed from its normal, inactive state to an excited state. In the excited state, the dyes pass their energy to oxygen molecules present in the surrounding blood and tissue cells of the body, creating a chemical radical called singlet oxygen. Singlet oxygen is toxic to cells because it oxidizes, or attacks, cellular structures, for example, and possibly, the cell membrane, mitochondria, lysosomal membrane, and the nucleus. When the accumulation of damage from oxidation exceeds a threshold level, the cell begins to die.

Evidence from tumor and CNV models indicate that occlusion, or blockage, of the vasculature is a major mechanism of PDT, which occurs after damage or death of the targeted cells, wherein platelet adhesion, degranulation and thrombus formation result.

After deciding to proceed with PDT treatment using photodynamic dyes, any of a number of available photodynamic dyes can be used. The dye selected should be capable of causing damage to the targeted tissue after exposure to the appropriate type of radiation, e.g., light of a certain wavelength, typically between about 630 nm and about 750 nm. A number of dyes that meet this criteria are presently available, and include, but are not limited to:

hematoporphyrins, which include derivatives thereof such as, e.g., dihematoporphyrin ethers and dimer and trimers of hematoporphyrins (examples of which are described in U.S. Pat. Nos. 4,968,715 and 5,190,966), and improvements thereon, examples of the latter being described in U.S. Pat. Nos. 5,028,621, 4,866,168, 4,649,151 and 5,438,071;

aminolevulinic acids (precursors to hematoporphyrin) as sources of photodynamic compounds, as described and exemplified in U.S. Pat. No. 5,079,262;

porphyrins, including boronated porphyrin, benzoporphyrin, and derivatives thereof, and as further exemplified by the green porphyrins described in U.S. Pat. Nos. 4,883,790, 4,920,143, 5,095,030 and 5,171,749;

merocyanines;

porphycenes;

porfimer sodium;

verteporfin (Vysudine™, CIBA Vision);

Photofrin II™;

PH-10™;

chlorins, as exemplified by meso-tetra(hydroxyphenyl)-chlorin and bacteriochlorins, the latter exemplified in U.S. Pat. Nos. 5,171,741, 5,173,504;

zinc phthalocyanine, as described in U.S. Pat. No. 5,166,197;

purpurins, such as tin ethyl etiopurpurin (SnET2™, Miravant);

pheophorbides, examples of which are described in U.S. Pat. Nos. 5,198,460, 5,002,962 and 5,093,349; and monoclonal antibody-dye conjugates of each of the foregoing, and, optionally;

mixtures of any or all of the foregoing.

Another patent that describes or identifies suitable photodynamic dyes is U.S. Pat. No. 5,910,510.

Several photodynamic dyes are currently approved by the FDA, or are in clinical trials, for use in treating cancer. For example, Photofrin® (porfimer sodium, manufactured by QLT PhotoTherapeutics and distributed by Sanofi Pharmaceuticals, Inc. and Beaufour Ipsen) is currently FDA-approved for early and late stage lung cancer and esophageal cancer. The following other photodynamic dyes are presently undergoing clinical trials and/or animal studies: Bopp® (boronated porphyrin, Pacific Pharmaceuticals) for brain cancer, Foscan® for head and neck cancer (Scotia QuantaNova), Lutrin™ for breast cancer (lutetium texaphyrin (Lu-Tex), Pharmacyclic) and PH-10 for cancerous tumors (Photogen Technologies, Inc.). PDT, using photodynamic dyes, is also undergoing clinical trials directed toward treating early-stage gastric and cervical cancers, skin cancers, arthritis, psoriasis, inflammatory bowel disease, cervical dysplasia, Antrin® for atherosclerosis (lutetium texaphyrin (Lu-Tex), Pharmacyclic) and macular degeneration.

The particular wavelength of light required to excite the aforesaid and other photodynamic dyes is readily available in the literature, and will not be recited herein.

The photodynamic dye may be administered by any method capable of delivering an effective amount of the dye to the targeted tissue, e.g., oral, parenteral, and rectal administration. Parenteral administration, such as IV and IM, is preferred.

The amount of dye that should be administered is that sufficient to provide an amount that which is capable, upon excitation, to damage the targeted tissue. This amount can vary widely depending upon the mode of administration and the formulation in which it is carried, e.g., liposomes, coupled to a target-specific ligand (such as an antibody or an immunologically-active fragment). As it is generally recognized that there is a relationship between the type of photodynamic dye, the formulation, mode of administration, and dosage level, adjustment of these parameters to fit the particular combination to ensure delivery of an effective amount of the dye formulation to the targeted tissue is possible.

Generally, the dosage for photodynamic dyes administered via IV for CNV treatment will typically range from about 0.1 mg/kg to about 20 mg/kg, advantageously range from about 0.5 mg/kg to about 10 mg/kg, and preferably range from about 1 mg/kg to about 5 mg/kg.

After the dye is administered, the application of dye excitation radiation, preferably via laser light, should be withheld until the targeted tissues selectively retain the dye. In other words, radiation application should be withheld until the dye concentration in the target tissue is relatively greater than the dye concentration in the non-target tissue. This will minimize damage to the non-targeted tissue. The optimum time following administration until the application of radiation to the treatment site will vary, and depends upon the mode of administration, the form of administration, and the nature of the targeted tissue should any radiation inadvertently be administered to non-targeted tissue. By way of example, if a CNV is the targeted tissue, the time between administration and application of radiation ranges from about 1 minute to about 2 hours, advantageously between about 5 to about 30 minutes, and preferably about 10–25 minutes.

The fluence and irradiation during the treatment with the radiation source can also vary, depending upon the type of tissue undergoing treatment, the depth of treatment desired in the targeted tissue, and the amount of overlying fluid or blood. Generally, however, the fluence will vary between about 50–200 joules/cm$^2$. The irradiance typically varies from about 150–900 mW/cm$^2$, with a range between about 150–600 mW/cm$^2$ being preferred. However, the use of a higher irradiance level may be preferable because higher levels shorten the treatment time.

While the treatment steps that comprise the inventive method are described herein in connection with the treatment of lesions generally, it should be appreciated that those steps are readily applicable to the treatment of specific types of lesions, e.g., CNVs and tumors. Of course, there are preferred means of completing those steps depending upon the particular types of lesion undergoing treatment. For example, one device used to assist in delivery of the radiation for PDT, photocoagulation, or both, may be preferred over another (a fundus camera with diode laser associated with fiber optic for CNV, an endoscope with fiber optic laser for tumors), as will the wavelength and other characteristics of the radiation being delivered, due to differences in dye properties (e.g., different photodynamic dyes, and differences between photodynamic dyes and dyes used in dye-enhanced photocoagulation). A further description of the use of an endoscope with the application of radiation under both PDT and thermal photocoagulation is provided below.

While the treatment steps described previously cause damage to the targeted tissue, the application of one or more further treatment steps in accordance with the methods of the present invention is desirable because additional damage to the tissue will result. More specifically, the methods of the present invention further contemplate applying radiation to a blood vessel that carries blood into the lesion. This radiation should be of a type and in an amount sufficient to increase the temperature of the feeder vessel, causing a subsequent reduction in the rate of blood flowing through that vessel. This step is generally referred to as thermal photocoagulation.

It should be appreciated that the further treatment step of thermal photocoagulation is preferably performed after the application of PDT when reperfusion of the CNV is detected, but it is not intended that the inventive methods be limited to that sequence. If reperfusion after PDT occurs, it typically is detectable 2–8 weeks after PDT. Thus, PDT and thermal photocoagulation need not be performed during a single treatment session. Days, or more likely weeks, could separate the PDT and thermal photocoagulation steps without departing from the spirit and scope of the present invention.

While not desiring to be bound to any particular theory, it is believed that the application of radiation to effect thermal photocoagulation, in the manner of the present invention, increases the temperature of the feeder vessel above normal body temperature, and thereby creates an environment that promotes vessel occlusion. Occlusion of the vessel under such conditions is expected to occur either by cauterization of the vessel, or by subsequent gradual clotting of the blood within the vessel. This clotting may be promoted by the damage caused to the vessel by the radiation, by the creation of a high temperature environment within the vessel that causes the blood to coagulate, or by a combination thereof.

The radiation to cause the foregoing occlusion will typically be light from a laser source, and may be used alone or in combination with a radiation-absorbing dye. Radiation-absorbing dyes are those that increase in temperature upon exposure to radiation of a particular wavelength. When used without a radiation-absorbing dye, the application of radiation to increase the temperature of the vessel may be referred to as thermal photocoagulation. When a radiation-absorbing dye is used, the application of radiation may be referred to as dye-enhanced thermal photocoagulation.

Certain radiation-absorbing dyes may also be classified as fluorescent dyes. Fluorescent dyes, as their name implies, fluoresce when exposed to radiation of a particular wavelength. Fluorescent dye are advantageously used in connection with a low-powered targeting laser light (not capable of effecting photocoagulation treatment) to obtain angiograms of the vasculature of interest. The low-powered laser light, applied at a certain wavelength, causes the dye to fluoresce, and thus illuminates the vasculature, and the targeted feeder vessels. Because the angiogram permits accurate targeting of the feeder vessel, the subsequent firing of the treatment laser should significantly increase the probability of effective treatment of the vessel.

Advantageously, therefore, a fluorescent dye is used to obtain angiograms of the vasculature of interest to permit accurate targeting, while a radiation-absorbing dye is used in dye-enhanced photocoagulation effect treatment of feeder vessels.

Accordingly, a second composition is administered to a subject prior to applying the treatment laser to effect thermal photocoagulation. This second composition includes, but is not limited to, a radiation-absorbing dye and a pharmaceutically-acceptable carrier. A sufficient amount of the second composition is administered so the targeted blood vessel is at least partially filled with the composition. Subsequently, radiation is applied to the blood vessel of a type and in an amount sufficient to cause the radiation-absorbing dye to increase the temperature of the blood, vessel and/or tissue adjacent the dye above normal body temperature. The temperature increase should be sufficient to promote partial, or preferably complete, occlusion of the vessel via one or more of the theorized mechanisms previously discussed.

The radiation-absorbing dyes useful in the dye-enhanced thermal photocoagulation steps of the present invention may be any dye that is able to generate a thermal response when exposed to radiation of an appropriate wavelength. As the correlation between radiation wavelength and increase in dye temperature is well known to those skilled in the art, this data will not be repeated herein. The radiation-absorbing dyes may also fluoresce, permitting the same dye to be used to obtain angiographic images of blood vessels, and treatment of vessels targeted as a result of the angiogram.

A number of radiation-absorbing dyes are known that are acceptable for use in the second composition of the inventive method. Exemplary radiation-absorbing dyes include fluorescein, rose bengal, indocyanine green (ICG) (IC-GREEN™, manufactured by Akom, Inc., Decatur, Ill.), analogue members of the tricarbocyanine dyes, and any other dye which meets the criteria described herein for photocoagulation treatment procedures. The preferred radiation-absorbing dye is ICG because it is readily available, has long been approved for administration to humans for ophthalmic angiography (because it is also a fluorescing dye) and other unrelated indications, and is suitable for treatment procedures. As the peak absorption and emission of ICG lies in the range of 800–850 nm, a light source emitting such wavelengths should be used when targeting vessels prior to the application of treatment radiation, as well as during the subsequent treatment step.

The second dye composition may further include a pharmaceutically-acceptable carrier. The carrier enhances the administration of the radiation-absorbing dye to a patient, the latter being either parenterally, preferably via IV injection, or by other suitable means. The choice of carrier will be determined in part by the particular radiation-absorbing dye used, as well as by the particular route of administration of the liquid composition. The carrier should be compatible with both the dye and the tissues and organs of the subject that come into contact with the liquid composition.

Illustrative of suitable carriers are water, saline, alcohols, red blood cells (RBC), glycerin, polyethylene glycol, propylene glycol, polysorbate 80, Tweens, liposomes, amino acids, lecithin, dodecyl sulfate, lauryl sulfate, phospholipid, Cremophor, desoxycholate, soybean oil, vegetable oil, safflower oil, sesame oil, peanut oil, cottonseed oil, sorbitol, acacia, aluminum monstearate, polyoxyethylated fatty acids, povidone and mixtures thereof. Advantageously, the carrier is water.

Optional components that may be present in either of the dye compositions used herein include tonicity and/or pH adjusters, e.g., NaOH, HCl, tribuffer phosphate, tris buffer and the like. In addition, the composition may include thrombin or other known blood clotting compounds that would function to further enhance blood clotting during and after photocoagulation treatment.

The compositions may initially be provided as a lyophilizate for reconstitution before use, or as a pre-mix, in a vial or syringe.

Liposomes may also be used in connection with the present invention as a carrier for the dyes. As technology providing for the formation of liposomes is well known, such will not be repeated herein. However, the following are illustrative of components that are expected to provide suitable dye-carrying liposomes: cholesterol, stearic acid, egg phosphotidyl choline, and stearyl amine.

When utilizing dye-enhanced photocoagulation, any suitable source of radiation that permits the particular radiation-absorbing dye to have the requisite thermal response as it flows through the vessels of interest may be used in the present methods. The type and amount of radiation applied to the blood vessels of interest must be sufficient to cause the radiation-absorbing dye present in these blood vessels to cause the blood and surrounding vessel to increase in temperature. The radiation applied to a vessel for treatment, of course, should be within the limits of the maximum flux density or irradiance which can be applied to the blood vessels of interest within a particular time span without causing excessive damage to the normal, untargeted, surrounding tissue. The longer the duration of exposure to the energy source, the lower the allowable level of irradiance. The particular energy source and amount of energy applied will depend upon the type of dye administered to the subject.

The radiation used in the thermal photocoagulation method described herein is preferably applied using laser optics. For treating ocular tumors or CNVs, various devices, preferably fundus cameras, can be adapted for providing an appropriate level and type of radiation in accordance with the teachings provided herein. The latter include, for example, those described in U.S. Pat. Nos. 5,279,298, 5,394,199 and 5,400,791. Preferably, a fundus camera having two sources of radiation (e.g., diode lasers) is provided. Using such a camera, one laser can be used to irradiate the general area of interest so any vessels requiring treatment can be identified via angiography using a suitable fluorescent dye, while the second relatively high-powered laser can be used almost immediately upon identification of the vessel to be treated to treat such vessel, either with or without the use of a radiation-absorbing dye. The ability of this methodology to permit the completion of thermal photocoagulation within minutes, e.g., advantageously in less than about 30 and preferably less than about 15 minutes, lessens patient trauma and increases overall treatment efficiency.

One method of determining the degree of vessel obstruction is by analyzing angiograms taken after treatment is completed. For example, if the treatment results in total obstruction of a CNV feeder vessel, an angiogram of the downstream portion of the vessel, e.g., the CNV itself, will not reveal any dye fluorescence. Partial obstruction should reveal a lower degree of fluorescence. X-ray, MRI or other scanning may also reveal a regression of the lesion after treatment.

As previously mentioned, the present invention contemplates the treatment of abnormal vasculature, e.g., lesions, at locations other than in the eye. Generally, the present invention permits the steps of PDT and thermal photocoagulation of blood vessels to be conducted at any location in an animal in which the required radiation can be effectively delivered. For example, tumors on the interior wall of the bladder, stomach, colon may be treated, as well as those on exterior walls of those organs.

An endoscope may advantageously be used to deliver the previously mentioned treatments for lesions, tumors, at location other then the eye, e.g., PDT and photocoagulation. For example in a preferred method wherein dye-enhanced photocoagulation is used, the endoscope would be inserted into the body and positioned adjacent the area of interest. A first instrument, typically a laser optic fiber, would be used with the endoscope to provide radiation at an appropriate wavelength to cause any of a previously administered fluorescent dye within the subject vessels to fluoresce, permitting identification of the vessel(s) to be treated. A second instrument would be used with the endoscope that would permit an angiographic image of the fluorescing dye within the vessels to be obtained. For example, an optical device connected to a CCD camera, such as those used to perform a colonoscopy and other invasive procedures to permit a physician to view the interior of a body cavity, presently exists, and such technology may be readily adapted for use in conjunction with the endoscopic procedures of the present invention.

After obtaining the angiogram and targeting the vessels of interest, a radiation-absorbing dye is advantageously administered, followed by application of radiation of a type and in an amount sufficient to cause the temperature of the dye, and thus the blood and surrounding targeted tissue, to increase, thereby affecting treatment of the targeted tissue. More specifically, treatment is preferably effected by applying radiation upstream of the abnormal vasculature, e.g., lesion, onto the feeder vessels to effect partial, or preferably total, occlusion of the vessel.

When treatment of a CNV is undertaken in accordance with the method of the present invention, the treatment may be accompanied by antioxidant therapy, e.g., administration of carotenoids such as lutein and zeaxanthin, by any suitable delivery means.

When the treatment of a tumor is undertaken, the method of the present invention is preferably used in combination with other treatment agents. For example, therapeutically-effective amounts of chemotherapeutic agents, such as cisplatin, carboplatin, doxorubicin, paclitaxel, taxotere, methotrexate, fluorouracil, camptothecin, cyclophosphamide and mixtures thereof, may be administered, as well as therapeutically-effective amounts of anti-angiogenesis agents, either alone or in combination, may be administered. The identity of suitable anti-tumor and antiangiogenesis agents (e.g., angiostatin and endostatin) and associated dosage regimens are well known, and as such will not be repeated herein. The administration of these agents may occur at any time, so long as the administration does not interfere with the treatment methods of the present invention. Advantageously, however, the agents may be administered in combination with the thermal photocoagulation treatment methods described herein. For example, the agents can be administered immediately after photocoagulation of tumor feeder vessels, and preferably are injected directly into the tumor. This provides several advantages including the reduction of trauma to the patient because multiple treatment agents are administered in a single procedure, the chemotherapeutic and anti-angiogenesis agents are delivered directly to the tumor thereby limiting the exposure of healthy tissue to these toxic agents (as would be the case using conventional IV administration), and conventional radiation can be narrowly focused on the tumor itself, as opposed to conventional methods that irradiate an area surrounding the tumor.

Conventional radiation treatment, mentioned previously, and surgical intervention, may also be used individually or in combination after the diagnostic methods of the present invention have been used, or alternatively in combination with the treatment methods of the present invention.

When diagnosis of the tumor is made in accordance with the angiogram methodology of the present invention, the location and boundaries of the tumor may be determined with a high degree of precision, without resort to the use of more harmful diagnostic procedures, e.g., X-rays. The precision provided by the present invention permits the treatment agents described previously to be more efficient because they are applied with a high degree of precision onto just the tumor itself, as compared to conventional methods, e.g., systemic administration of chemotherapeutic agents and application of radiation, which are applied over a more general area. This precise focus, in turn, lessens trauma to the subject by minimizing the side effects of these toxic agents.

All of the references cited herein, including patents, patent applications, and publications, are hereby incorporated in their entireties by reference.

Further, and unless otherwise indicated, references to a single component, structure or step herein should be construed as also including more than one such component, structure or step, i.e., at least one or one or more.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A method for treating a lesion of an animal, the animal having a blood vessel that carries blood into the lesion, comprising
    (a) administering a first composition comprising a dye suitable for use in photodynamic therapy and a pharmaceutically-acceptable carrier to the animal to fill at least a portion of the lesion with the first composition;
    (b) applying radiation to the lesion of a type and in an amount sufficient to excite the dye residing therein and cause the lesion to undergo photodynamic therapy;
    (c) administering a second composition comprising a dye suitable for use in dye-enhanced photocoagulation and a pharmaceutically-acceptable carrier to the animal to fill at least part of the blood vessel that carries blood into the lesion; and
    (d) applying radiation to the blood vessel as the second composition at least partially fills the vessel of a type and in an amount sufficient to excite the dye therein, thereby reducing the rate of blood flow through the vessel.

2. The method according to claim 1, wherein the dye suitable for use in dye-enhanced photocoagulation is selected from the group consisting of indocyanine green, fluorescein, rose bengal, lutetium texaphyrin and mixtures thereof.

3. The method according to claim 1, wherein the application of radiation to the blood vessel during step (d) is of a type and in an amount sufficient to cause the vessel to at least partially collapse.

4. The method according to claim 1, wherein the radiation applied to the blood vessel during step (d) is of a type and in an amount sufficient to increase the temperature of the blood to a level that promotes clotting of blood in the vessel.

5. The method according to claim 1, wherein radiation is applied in step (b) using an endoscope.

6. The method according to claim 5, wherein radiation is application in step (d) using an endoscope.

7. The method according to claim 1, wherein the blood vessels feeding the lesion are in tissue which defines a body cavity.

8. The method according to claim 7, wherein the tissue is located in the eye, lung, gastrointestinal tract, bladder, pancreas, gall bladder, sinus, heart, cervix, brain, ovary, prostate, stomach or skin.

9. The method according to claim 1, wherein the dye useful for photodynamic therapy is selected from the group consisting of hematoporphyrins, aminolevulinic acids, porphyrins, merocyanines, porphycenes, verteporfin, porfimer sodium, PH-10, Photofrin II, chlorins, zinc phthalocyanine, purpurins, pheophorbides, monoclonal antibody conjugates of any of the foregoing dyes, and mixtures thereof.

10. The method according to claim 1, wherein the lesion is a CNV.

11. The method according to claim 1, wherein steps (c) and (d) are completed within 6 months of the completion of steps (a) and (b).

12. The method according to claim 11, wherein steps (a)–(d) are completed within 8 weeks.

13. The method according to claim 1, wherein steps (c) and (d) are performed prior to steps (a) and (b).

14. The method according to claim 1, wherein the radiation is applied in step (d) using an endoscope.

15. The method according to claim 14, wherein the radiation is applied in step (b) using an endoscope.

16. A method for treating a lesion of an animal, the animal having a blood vessel that carries blood into the lesion, comprising
(a) administering a first composition comprising a dye suitable for use in photodynamic therapy selected from the group consisting of hematoporphyrins, aminolevulinic acids, porphyrins, merocyanines, porphycenes, verteporfin, porfimer sodium, PH-10, Photofrin II, chlorins, zinc phthalocyanine, purpurins, pheophorbides, monoclonal anti-body conjugates of any of the foregoing dyes, and mixtures thereof and a pharmaceutically-acceptable carrier to the animal to fill at least a portion of the lesion with the first composition;
(b) applying radiation to the lesion of a type and in an amount sufficient to excite the dye residing therein and cause the lesion to undergo photodynamic therapy;
(c) administering a second composition comprising a dye selected from the group consisting of indocyanine green, fluorescein, rose bengal, lutetium texaphyrin and mixtures thereof and a pharmaceutically-acceptable carrier to the animal to at least partially fill the blood vessel that carries blood into the lesion with the second composition; and
(d) applying radiation to the blood vessel as the second composition at least partially fills the vessel of a type and in an amount sufficient to excite the dye therein and thereby reduce the rate of blood flow through the vessel.

17. The method according to claim 11, wherein steps (c) and (d) are performed prior to steps (a) and (b).

18. A method for treating CNV in an animal, the animal having a blood vessel that carries blood into the CNV, comprising
(a) administering a first composition comprising a dye suitable for use in photodynamic therapy and a pharmaceutically-acceptable carrier to the animal to fill at least part of the CNV with the first composition;
(b) applying radiation to the CNV of a type and in an amount sufficient to excite the dye residing therein and cause the lesion to undergo photodynamic therapy;
(c) administering a second composition comprising a dye suitable for use in dye-enhanced photocoagulation and a pharmaceutically-acceptable carrier to the animal to fill at least part of the blood vessel that carries blood into the CNV with the second composition; and
(d) applying radiation to the blood vessel as the second composition at least partially fills the vessel of a type and in an amount sufficient to excite the dye therein, thereby reducing the rate of blood flow through the vessel.

19. The method according to claim 18, wherein steps (c) and (d) are performed after step (b), and after reperfusion of the CNV.

20. The method according to claim 18, wherein steps (c) and (d) are completed within 6 months of the completion of steps (a) and (b).

21. The method according to claim 20, wherein steps (a)–(d) are completed within 8 weeks.

22. The method according to claim 13, wherein steps (c) and (d) are performed prior to steps (a) and (b).

23. A method for damaging a tumor in an animal, the animal having a blood vessel that carries blood into the tumor, comprising
(a) administering a first composition comprising a dye suitable for use in photodynamic therapy and a pharmaceutically-acceptable carrier to the animal to fill at least a part of the tumor with the first composition;
(b) applying radiation to the tumor of a type and in an amount sufficient to excite the dye residing therein and cause the lesion to undergo photodynamic therapy, wherein the tumor is damaged;
(c) administering a second composition comprising a dye suitable for use in dye-enhanced photocoagulation and a pharmaceutically-acceptable carrier to the animal to fill at least part of the blood vessel that carries blood into the tumor; and
(d) applying radiation to the blood vessel as the second composition at least partially fills the vessel of a type and in an amount sufficient to excite the dye therein, thereby reducing the rate of blood flow through the blood vessel.

24. The method according to claim 23, wherein the dye useful for photodynamic therapy is selected from the group consisting of hematoporphyrins, aminolevulinic acids, porphyrins, merocyanines, porphycenes, verteporfin, porfimer sodium, PH-10, Photofrin II, chlorins, zinc phthalocyanine, purpurins, pheophorbides, monoclonal anti-body conjugates of any of the foregoing dyes, and mixtures thereof.

25. The method according to claim 24, wherein the dye suitable for use in dye-enhanced photocoagulation is selected from the group consisting of indocyanine green, fluorescein, rose bengal, lutetium texaphyrin and mixtures thereof.

26. The method according to claim 15, wherein radiation is applied in step (b) using an endoscope.

27. The method according to claim 26, wherein radiation is applied in step (d) using an endoscope.

28. The method according to claim 23, wherein the application of radiation to the blood vessel during step (d) is of a type and in an amount sufficient to cause the vessel to at least partially collapse.

29. The method according to claim 23, wherein the radiation applied to the blood vessel during step (d) is of a type and in an amount sufficient to increase the temperature of the blood to a level that promotes clotting of blood in the vessel.

30. The method according to claim 23, wherein the tumor is in tissue which defines a body cavity.

31. The method according to claim 30, wherein the tissue is located in the eye, lung, gastrointestinal tract, bladder, pancreas, gall bladder, sinus, heart, cervix, brain, ovary, prostate, stomach or skin.

32. The method of claim 23, further comprising administering an effective amount of a chemotherapeutic agent.

33. The method of claim 32, wherein the administration is effected by injecting the chemotherapeutic agent directly into the tumor.

34. The method of claim 23, further comprising administering an effective amount of an anti-angiogenesis agent.

35. The method of claim 34, wherein the administration is effected by injecting the anti-angiogenesis agent directly into the tumor.

36. The method of claim 23, further comprising administering radiation of a type and in an amount effective to reduce the size of the tumor.

37. The method according to claim 15, wherein radiation is applied in step (b) using an endoscope.

38. The method according to claim 29, wherein radiation is applied in step (d) using an endoscope.

39. The method according to claim 15, wherein steps (c) and (d) are completed within 6 months of the completion of steps (a) and (b).

40. The method according to claim 15, wherein steps (a)–(d) are completed within 8 weeks.

41. The method according to claim 15, wherein steps (c) and (d) are performed prior to steps (a) and (b).

* * * * *